US00PP25983P3

(12) United States Plant Patent
Zaiger et al.

(10) Patent No.: US PP25,983 P3
(45) Date of Patent: Oct. 13, 2015

(54) ***NECTARINE* TREE NAMED 'HONEY SPRING'**

(50) Latin Name: ***Prunus persica* var. *nucipersica***
Varietal Denomination: Honey Spring

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 72 days.

(21) Appl. No.: 13/999,483

(22) Filed: Mar. 4, 2014

(65) Prior Publication Data

US 2015/0257318 P1 Sep. 10, 2015

(51) Int. Cl.
*A01H 5/00* (2006.01)

(52) U.S. Cl.
USPC ..... Plt./190

(58) Field of Classification Search
USPC ..... Plt./190
See application file for complete search history.

*Primary Examiner* — Annette Para

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Regular and heavy production of large size fruit.
3. Fruit with firm, yellow flesh, good handling and shipping qualities.
4. Fruit with very good flavor.
5. Fruit with attractive red skin color.

1 Drawing Sheet

Botanical designation: *Prunus persica* var. *nucipersica*.
Variety denomination: 'HONEY SPRING'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricot, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein, 'Honey May' Nectarine (U.S. Plant Pat. No. 19,363) and our proprietary nectarine selections '387LU177' '58ZA720' and '396LN445'.

STATEMENT REGARDING FEDERALLY SPONSORED RESEARCH AND DEVELOPMENT

Not applicable.

ORIGIN OF THE VARIETY

A new and distinct variety of nectarine tree (*Prunus persica* var. *nucipersica*) was originated by us in our experimental orchard located near Modesto, Calif. as an open pollinated seedling from our proprietary nectarine seedling with the field identification number '387LU177'. The seed parent (387LU177) originated as a first generation seedling from a cross between our proprietary seedlings with the field identification numbers '58ZA720' and '396LN445'. A large group of these open pollinated seedlings were planted and maintained on their own root system, during which time we recognized the desirable tree and fruit characteristics and selected it in 2007 for asexual reproduction and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree is of large size, vigorous, upright growth and a productive bearer of large size, yellow flesh, clingstone fruit. The fruit is further characterized by having firm flesh, very good flavor and eating quality, with an attractive red skin color. In comparison to its seed parent (387LU177) the fruit of the new variety is firmer, larger in size and is approximately 15 days later in maturity. In comparison to the commercial nectarine 'Honey May' (U.S.

Plant Pat. No. 19,363) the fruit of the new variety is larger in size and is approximately 30 days later in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 6 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, growth of approximately 1.5 meters in height the first growing season. Varies with soil type, fertility and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desirable market size. Number of fruit set varies with climatic conditions during blooming period.

*Bearer*.—Regular, adequate fruit set 5 consecutive years. No alternate bearing observed.

*Fertility*.—Self-fertile.

*Density*.—Medium dense, usually pruned to vase shape to increase air movement and sunlight to the center of the tree to enhance health of tree and improved fruit color.

*Hardiness*.—Hardy in all stone fruit growing areas of California. Tree grown in USDA Hardiness Zone 9. Winter chilling requirement approximately 250 hours at or below 45° F.

Trunk:

*Size*.—Medium. Average circumference 33.0 cm at 25.4 cm above ground on a 6 year old tree.

*Stocky*.—Medium stocky.

*Texture*.—Medium shaggy, becomes rougher with age.

*Color*.—Varies from 2.5Y 5/2 to 5Y 4/2.

Branches:

*Size*.—Medium. Average circumference 10.2 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 20 in a 25.8 sq cm area. Average length 3.3 mm. Average width 1.8 mm. Color varies from 7.5YR 5/6 to 10YR 7/8.

*Color*.—New growth varies from 5GY 5/8 to 10R 3/6 where exposed to sun. Mature growth varies from 7.5YR 2/4 to 10YR 7/8, varies with age of growth.

Leaves:

*Size*.—Medium to large. Average length 119.7 mm. Average width 38.8 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, small ridges created by midrib and pinnate venation. Both surfaces glabrous.

*Petiole*.—Average length 8.8 mm. Average width 1.4 mm. Longitudinally grooved. Surface glabrous. Color varies from 2.5GY 5/8 to 5GY 5/6.

*Glands*.—Reniform. Size — small to medium. Average length 1.1 mm. Average diameter 0.6 mm. Average number 3, varies from 1 to 4. Located primarily on the base of the leaf blade and on the upper portion of the petiole. Color varies from 10Y 6/8 to 2.5GY 7/8.

*Stipules*.—Present, average number 2. Average length 5.8 mm. Margin — pectinate. Color 2.5GY 6/8.

*Color*.—Upper surface varies from 7.5GY 3/4 to 5GY 3/6. Lower surface varies from 5GY 4/4 to 7.5GY 4/4. Midvein color varies from 2.5GY 7/8 to 5GY 7/6.

Flower buds:

*Size*.—Medium to large. Average length 18.9 mm. Average diameter 11.7 mm.

*Hardiness*.—Hardy with respect to California winters.

*Form*.—Conical, becoming elongated before opening.

*Pedicel*.—Average length 4.8 mm. Average width 0.8 mm. Color varies from 5GY 7/6 to 5GY 6/6.

*Color*.—Varies from 5RP 7/8 to 5RP 7/10.

Flowers:

*Blooming period*.—Date of First Bloom Feb. 14, 2013. Date of Petal Fall Feb. 24, 2013, varies slightly with climatic conditions.

*Size*.—Medium to large, showy. Average height 18.4 mm. Average diameter 34.0 mm.

*Petals*.—Normally 5, alternately arranged to sepals. Average length 17.2 mm. Average width 15.2 mm. Form — orbicular, narrows at point of attachment. Margin — sinuate. Color varies from 5RP 8/6 to 5RP 7/6. Both surfaces glabrous. Arrangement — free.

*Sepals*.—Normally 5, alternately arranged to petals. Average length 5.3 mm. Average width 5.3 mm. Shape — ovate. Margin — entire. Surface — upper surface glabrous, lower surface pubescent. Color — upper surface varies from 5GY 5/6 to 5R 3/8. Lower surface varies from 2.5R 3/2 to 2.5R 2/4.

*Stamens*.—Average number per flower 34. Average filament length 14.2 mm. Filament color varies from N 9.5/(white) to 7.5R 8/4. Anther color varies from 5Y 8/10 to 5R 4/10.

*Pollen*.—Self-fertile. Color varies from 2.5Y 7/12 to 2.5Y 6/10.

*Pistil*.—Normally 1. Surface — glabrous. Average length 18.5 mm. Position of stigma an average of 1.8 mm above anthers. Color varies from 10Y 8/4 to 10Y 8/6.

*Fragrance*.—Slight.

*Color*.—Varies from 5RP 8/6 to 7.5RP 7/6.

*Number flowers per flower bud*.—Normally 1.

*Pedicel*.—Average length 6.0 mm. Average width 1.2 mm. Color varies from 10Y 7/6 to 2.5GY 6/6.

Fruit:

*Maturity when described*.—Firm ripe.

*Date of first picking*.—Jun. 1, 2013.

*Date of last picking*.—Jun. 8, 2013, varies slightly with climatic conditions.

*Size*.—Large. Average diameter axially 61.5 mm. Average transversely in suture plane 69.8 mm. Average weight 181.8 grams, varies slightly with fertility of the soil, amount of thinning and climatic conditions.

*Form*.—Globose.

*Suture*.—Nearly smooth, extends from base to apex.

*Ventral surface*.—Smooth to very slightly lipped.

*Apex*.—Slightly retuse.

*Base*.—Retuse.

*Stem cavity*.—Rounded to slightly elongated in suture plane. Average depth 9.9 mm. Average diameter 12.0 mm.

Stem:

*Size*.—Medium. Average length 11.7 mm. Average diameter 2.7 mm.

*Color*.—Varies from 5YR 3/6 to 5GY 5/8.

Skin:

*Thickness*.—Medium.

*Surface*.—Smooth to very slightly waffled.

*Pubescence*.—Wanting.

*Tendency to split*.—None.

*Color*.—Ground color varies from 10YR 8/8 to 10YR 8/6, overspread with 7.5R 3/10 to 7.5R 3/14.

*Tenacity*.—Tenacious to flesh.

*Astringency*.—None.

Flesh:

*Ripens*.—Evenly.

*Texture*.—Firm, meaty.

*Fibers*.—Few, small, tender.

*Firmness*.—Firm, comparable to most commercial varieties.

*Aroma*.—Moderate.

*Amydgalin*.—Undetected.

*Eating quality*.—Very good.

*Flavor*.—Very good, mild, sweet and low acid.

*Juice*.—Moderate amount, enhances flavor.

*Brix*.—Average Brix 15.0°, varies slightly with amount of fruit per tree and climatic conditions.

*Color*.—Varies from 2.5Y 7/8 to 2.5Y 7/10.

*Pit cavity*.—Average length 32.6 mm. Average width 29.3 mm. Average depth 12.2 mm. Color varies from 5Y 7/8 to 5Y 7/10.

Stone:

*Type*.—Clingstone.

*Size*.—Large. Average length 31.6 mm. Average width 28.3 mm. Average thickness 22.4 mm.

*Form*.—Obovoid.

*Base*.—Flat.

*Apex*.—Rounded.

*Surface*.—Pitted throughout, pits vary from round to elongated.

*Sides*.—Unequal, one side extending further from suture plane.

*Ridges*.—Extend from base to apex.

*Tendency to split*.—None.

*Color*.—Varies from 7.5YR 5/8 to 7.5YR 6/8 when dry.

Kernel:

*Size*.—Large. Average length 17.3 mm. Average width 13.2 mm. Average depth 9.0 mm.

*Form*.—Ovate.

*Viability*.—Partially viable, some embryos not completely developed.

*Skin color*.—Varies from 5Y 8/6 to 5Y 8/8.

Use: Dessert. Market — local and long distance.

Keeping quality: Good, held firm 3 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, substantially as illustrated and described.

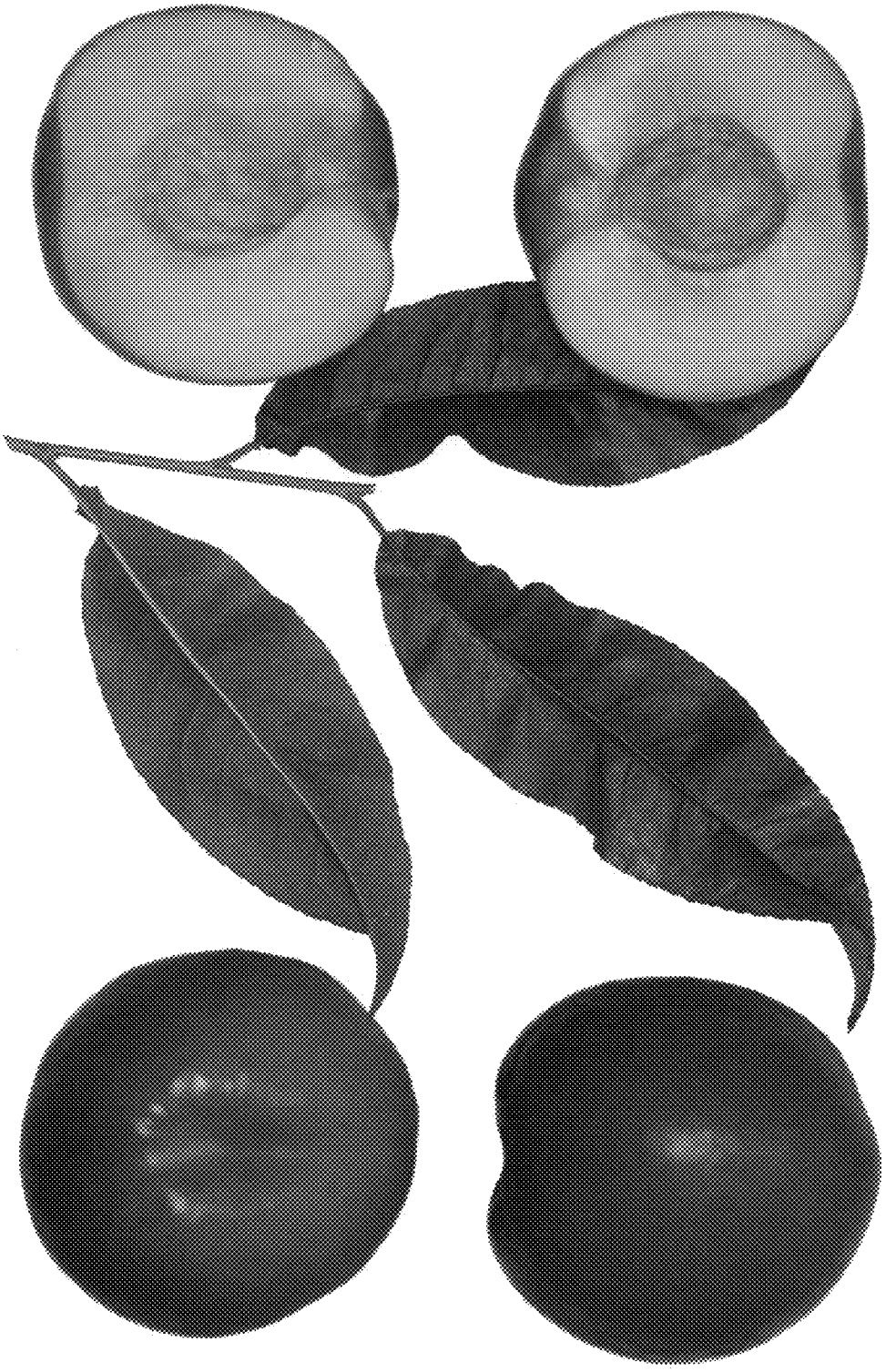

* * * * *